US007163618B2

(12) United States Patent
Beckham et al.

(10) Patent No.: US 7,163,618 B2
(45) Date of Patent: *Jan. 16, 2007

(54) MULTI-INLET PORT MANIFOLD FOR A MEDICAL WASTE RECEIVER HAVING AN ELEVATED FILTER ELEMENT AND TETHERED INLET PORT CAPS

(75) Inventors: Scott Beckham, Newport Beach, CA (US); Dale Emis, Mission Viejo, CA (US); Nilesh Patel, Laguna Niguel, CA (US)

(73) Assignee: Stryker Corporation, Kalamazoo, MI (US)

( * ) Notice: Subject to any disclaimer, the term of this patent is extended or adjusted under 35 U.S.C. 154(b) by 160 days.

This patent is subject to a terminal disclaimer.

(21) Appl. No.: 10/413,594

(22) Filed: Apr. 14, 2003

(65) Prior Publication Data

US 2003/0213733 A1  Nov. 20, 2003

Related U.S. Application Data

(62) Division of application No. 09/860,694, filed on May 21, 2001, now abandoned, which is a division of application No. 09/566,491, filed on May 8, 2000, now Pat. No. 6,331,246.

(51) Int. Cl.
*B01D 29/56* (2006.01)
(52) U.S. Cl. .............. 210/136; 210/335; 210/473; 137/602; 604/317
(58) Field of Classification Search ........... 222/145.1, 222/145.7; 137/602–607; 422/101; 210/449, 210/459–463, 136, 335, 473; 604/317
See application file for complete search history.

(56) References Cited

U.S. PATENT DOCUMENTS

| 110,136 | A | | 12/1870 | Hemenway |
| 493,378 | A | | 3/1893 | Gibson |
| 1,930,590 | A | * | 10/1933 | Ebinger ............... 137/505 |
| 24,255 | A | | 12/1956 | Lund |
| 3,060,882 | A | | 10/1962 | Peters et al. |
| 3,084,634 | A | * | 4/1963 | McDougall ............ 417/163 |
| 3,260,462 | A | * | 7/1966 | Smaczny ............... 239/33 |
| 3,415,485 | A | | 12/1968 | Hirs et al. |
| 27,399 | A | | 6/1972 | Urso |
| 3,773,256 | A | * | 11/1973 | Wright ................. 239/1 |
| 3,780,867 | A | * | 12/1973 | Zirlis ................. 210/266 |
| 4,067,696 | A | * | 1/1978 | Curtis ................. 422/47 |
| 4,141,379 | A | | 2/1979 | Manske ............... 137/496 |
| 4,226,344 | A | * | 10/1980 | Booth et al. ........... 222/504 |
| 4,298,475 | A | * | 11/1981 | Gartner ............... 210/266 |
| 4,322,054 | A | | 3/1982 | Campbell .............. 251/5 |
| 4,443,336 | A | | 4/1984 | Bennethum ............ 210/238 |
| 4,642,089 | A | * | 2/1987 | Zupkas et al. .......... 604/6.09 |
| 4,655,754 | A | | 4/1987 | Richmond et al. |

(Continued)

FOREIGN PATENT DOCUMENTS

WO   WO 99/33501   7/1999

*Primary Examiner*—Terry K. Cecil

(57) ABSTRACT

A filter system especially useful in the treatment of waste material, in particular liquid waste material which may include particulate matter therein. The filter system includes a series of filters of progressively finer porosity in order to selectively eliminate particulate (or semi-particulate) matters from a carrier material, typically but not exclusively, of a fluid or liquid nature. The filters are mounted within a housing which includes an outlet port and a plurality of inlet ports, wherein each inlet port includes a check valve.

14 Claims, 6 Drawing Sheets

U.S. PATENT DOCUMENTS

| | | |
|---|---|---|
| 4,735,610 A | 4/1988 | Akkas et al. ............... 604/119 |
| 4,915,688 A | 4/1990 | Bischof, deceased et al. |
| 4,957,492 A | 9/1990 | McVay |
| 4,999,109 A | 3/1991 | Sabre |
| 5,251,664 A | 10/1993 | Arvidsson et al. .......... 137/514 |
| 5,637,103 A | 6/1997 | Kerwin et al. .............. 604/317 |
| 5,914,047 A | 6/1999 | Griffiths .................... 210/739 |
| 5,945,004 A | 8/1999 | Ohira et al. ................ 210/710 |
| 5,971,956 A | 10/1999 | Epstein ...................... 604/119 |
| 6,024,720 A | 2/2000 | Chandler et al. ............. 604/35 |
| 6,083,205 A | 7/2000 | Bourne et al. ............. 604/246 |
| 6,139,757 A * | 10/2000 | Ohmura et al. ............ 210/797 |
| 6,149,812 A | 11/2000 | Erickson .................... 210/521 |
| 6,180,000 B1 | 1/2001 | Wilbur et al. ................ 210/85 |
| 6,244,311 B1 | 6/2001 | Hand et al. ................. 141/375 |
| 6,331,246 B1 * | 12/2001 | Beckham et al. .......... 210/136 |

\* cited by examiner

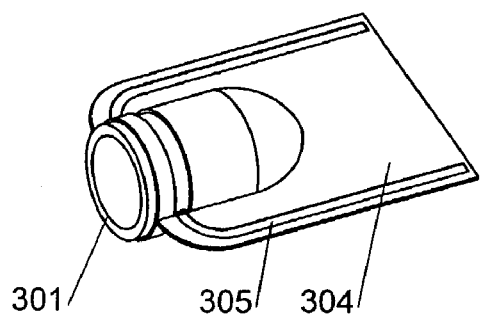
Fig. 6
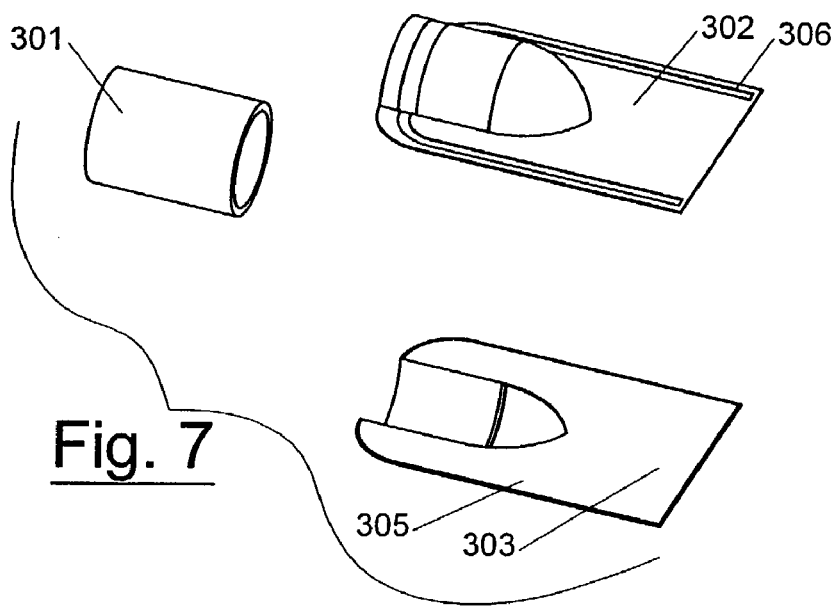
Fig. 7
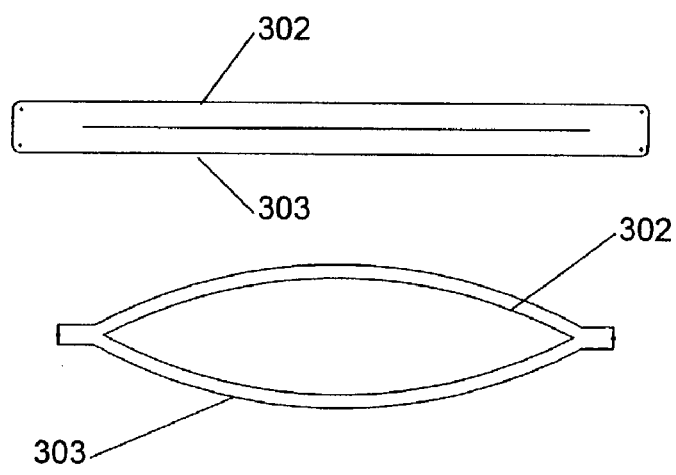
Fig. 8A
Fig. 8B

US 7,163,618 B2

MULTI-INLET PORT MANIFOLD FOR A MEDICAL WASTE RECEIVER HAVING AN ELEVATED FILTER ELEMENT AND TETHERED INLET PORT CAPS

RELATED APPLICATIONS

This application is a divisional of application Ser. No. 09/860,694, filed May 21, 2001, now abandoned, which is a divisional of application Ser. No. 09/566,491, filed May 8, 2000, now U.S. Pat. No. 6,331,246.

FIELD OF THE INVENTION

This invention is directed to a waste filter and manifold system, in general, and, more particularly, to a waste filter and manifold system for removing solids or semi-solids from a fluid or liquid carrier.

BACKGROUND OF THE INVENTION

There are many uses for waste filter and manifold systems and/or devices for removing certain types of materials from a carrier. One such application is the removal of solid or semi-solid detritus such as bone chips, flesh, blood clots, or the like from the waste material generated by a medical procedure or operation. This removal process permits the liquid or fluid carrier to be treated separately from the other debris which is trapped by the filtration process. Of course, filtration processes are not limited to the medical field, per se, but can be used in areas such as clean rooms or other sterile environments.

BRIEF SUMMARY OF THE INVENTION

The invention relates to a waste filter and manifold system which is especially useful in the treatment of waste material, in particular liquid waste material which may include particulate matter therein. The waste filter and manifold system includes filtration means, for example, a series of filter elements of increasingly finer porosity in order to selectively eliminate particulate and/or semi-particulate matter from a fluid or liquid carrier material passing through the filter elements. The filter elements are mounted within a housing which includes at least one inlet port and at least one outlet port. The waste filter and manifold system includes at least one check valve to establish unidirectional flow to prevent reverse flow of effluent therethrough. The filter elements are intended (but are not required) to be disposable. The housing may also be disposable, if preferred.

BRIEF DESCRIPTION OF THE SEVERAL VIEWS OF THE DRAWINGS

FIG. 6 is an oblique view of a check valve shown in FIG. 2 and used in the waste filter and manifold system of the instant invention;

FIG. 7 is an exploded view of the check valve shown in FIG. 6; and

FIGS. 8A and 8B show a distal end of the check valve shown in FIG. 6 illustrating closed and open positions, respectively.

DETAILED DESCRIPTION OF THE INVENTION

Figure 1:
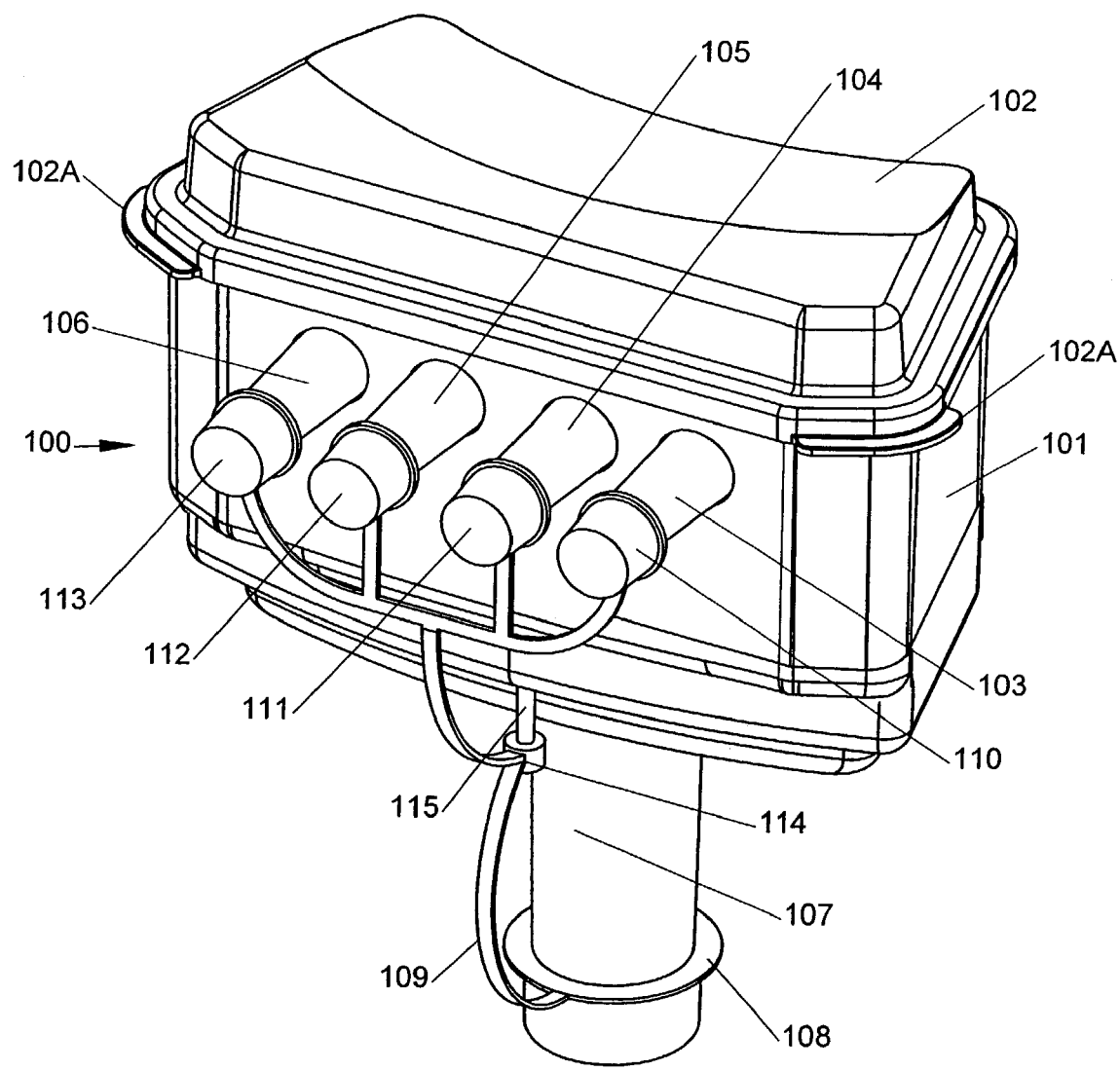
FIG. 1 is an oblique view of one embodiment of a housing for a waste filter and manifold system of the instant invention.

Referring now to FIG. 1, there is shown an oblique, external view of a preferred embodiment of a waste filter and manifold system 100 of the instant invention. The waste filter and manifold system 100 may also be referred to as a filtration unit 100 or simply as the system 100. The system 100 includes a generally hollow housing 101 defined by a number of side walls, (not identified) that extend upwardly from a base 150. A removable lid 102 is disposed over the open top of housing 101. The lid 102 can include one or more ears 102A, which are useful in removing the lid from the housing. Collectively, housing 101 and lid 102 form the head 151 of manifold system 100.

A plurality of inlet ports 103–106 are shown projecting outwardly from a front surface of the housing 101. As will be noted infra, the inlet ports 103–106 can be integrally formed with the housing 101. Alternatively, the inlet ports 103–106, the number of which is not a critical part of the invention, per se, be formed as a separate assembly which is conveniently mounted at the housing 101 (see infra at FIG. 2). The inlet ports 103–106 are provided to be connected to a suitable source of material to be filtered by means of a suitable conduit. In a typical application, the conduit comprises conventional "plastic" tubing, such as the plastic tubing through which medical waste material are evacuated.

As shown in this embodiment, an outlet stem 107 depends extends from a bottom of the housing head base 150. Stem 107 is formed with a through bore 152 through which drains the filtered contents of manifold head 150 into a suitable receiver, such as a medical waste receiver 156 shown as a block element in FIG. 3. Again, while not intended to be limitative of the invention, the outlet stem 107 is inserted into a conduit 158 integral with the receiver 156 such as conventional tubing. The manifold base 150 is formed with an opening 160 through which the waste material is able to flow into stem bore 152. The stem 107 has an outer circumference less than that of the head of the manifold. Stem bore 152 has a diameter smaller in area then the cross sectional area of the void space internal to manifold head 151. Opening 160 in base 150 of the manifold head 151 similarly has a smaller surface area then the cross sectional area of the head void space.

A feature of the system 100 comprises port caps 110–113 which fit snugly over outer ends of the inlet ports 103–106, respectively. In this embodiment, the port caps 110–113 are tethered together and to manifold housing 101 by a flexible cap leash 109. The configuration of the leash 109, typically a thin plastic strip, can vary as a function of design preference. In this embodiment, the leash 109 includes a cap ring 108 which is adapted to encircle and engage the outlet stem 107 for convenience. In addition, the leash 109 includes a leash grommet 114 which is adapted to engage a leash pin 115 which depends from a lower front portion of the housing 101. In this embodiment, the leash grommet 114 and cap ring 108 are formed as an integral unit.

In use, the port caps 110–113 are used to cover any of the inlet ports 103–106 which are not connected to an input source (not shown) as described supra, in order to maintain the integrity of the system 100, in general, and to prevent leakage through the housing 101, in particular. The port caps 110–113 can, of course, be individually provided (with or without individual leashes) and need not be connected by a common leash 109.

Figure 2:
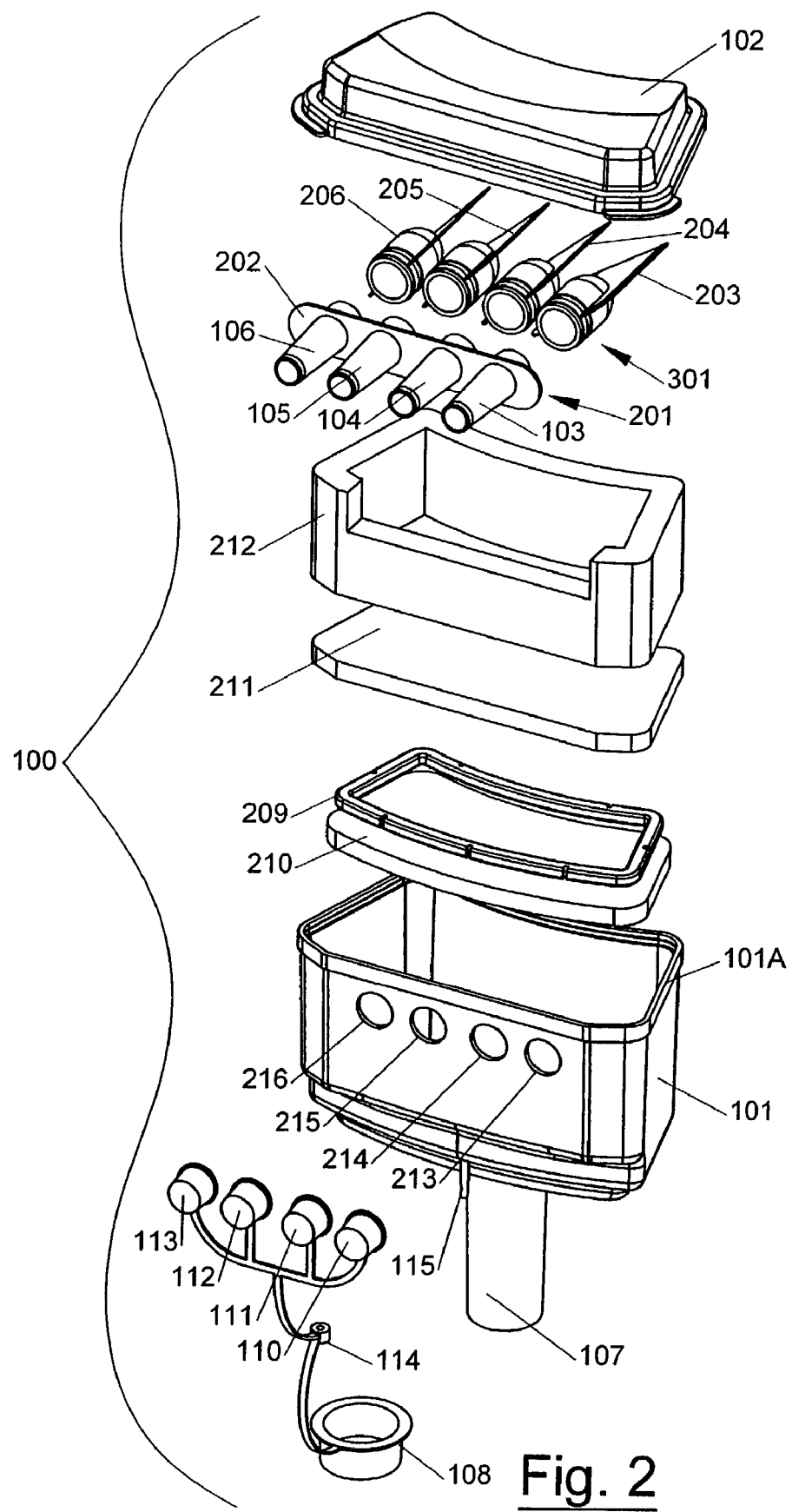
FIG. 2 is an exploded view of one embodiment of the waste filter and manifold system of the instant invention.

Referring now to FIG. 2 there is shown an exploded view of the system 100. Typically, the lid 102 is formed of polyethylene and includes a peripheral groove 102B (see infra at FIG. 3) which receives and snugly engages an upper edge 101A or lip of the housing 101. In this embodiment, the housing 101 is formed of ABS and is, generally, rectangular in configuration with a slightly arcuate rear surface (which is provided for mounting purposes in one typical application).

In this embodiment, a plurality of inlet port openings 213–216 are provided through the front surface of the housing 101. That is, as suggested supra, the inlet ports 103–106 can be formed on a common support base 202, and take the form of a separate assembly 201. In this case, the assembly 201 is placed inside the housing 101 with the proximal ends of the inlet ports 103–106 extending outwardly through the ports openings 213–216. The support base 202 is, typically, affixed to an inner surface of the housing 101 in any suitable manner. Of course, in the embodiment wherein the inlet ports 103–106 are formed as integral parts of the housing 101, per se, the separate port openings 213–216 are unnecessary.

The port caps 110–113 and the related cap leash 109, cap ring 108, and leash grommet 114 are adapted to be mounted to the assembly 201 as suggested in FIG. 1 whether the inlet ports 103–106 are separate or integral with the housing 101. Again, the leash 109 (and the design thereof) is not a critical portion of the invention.

A plurality of check valves 203–206 are adapted to be attached to inner or distal ends of the inlet ports 103–106, respectively. Each of the check valves 203–206, described in greater detail infra, includes a connection portion, for example connector 301, (generally cylindrical in this embodiment) which is the proximal end of the check valve and is adapted to be snugly joined to the inner (distal) end of the respective inlet port 103–106. A flexible distal end of each of the check valves 203–206 permits fluid flow through the check valves 203–206 in one direction only as described infra relative to FIGS. 6, 7, 8A, and 8B.

Mounted within the housing 101 is a first filter element 210 which is the least porous filter element in the preferred embodiment. Typically, the first filter element 210 is fabricated of reticulated polyurethane foam and is, in a preferred embodiment, about 0.3 inches thick. In this embodiment, the first filter element 210 has approximately 100 pores per linear inch although this parameter can vary in accordance with the application of the system 100.

Mounted within the housing 101 immediately above the first filter element 210 is a filter support gasket 209 which is fabricated of ABS and, thus, provides a rather rigid gasket. Typically, the gasket 209 conforms somewhat snugly to an inner perimeter of the housing 101. The gasket 209 is, typically, affixed to the inner surface of the housing 101 by any suitable method such as adhesives, bonding, frictional force fit, sonic welding, or the like. Thus, the gasket 209 maintains the first filter element 210 in position and prevents leakage flow to the outlet port 107 around the first filter element 210.

Mounted above the first filter element 210 is a second filter element 211 wherein the second filter element 211 is typically more porous than the first filter element 210. In the preferred embodiment, the second filter element 211 contains about 30 pores per linear inch and is about 0.3 inches thick. The second filter element 211 is, typically, fabricated of reticulated polyurethane foam and extends snugly to the inner surface of the housing 101 to prohibit flow therearound. The second filter element 211 tends to rest loosely upon the support gasket 209 and an upper surface of the first filter element 210.

Also, mounted in the housing 101 is a third filter element 212 which is the most porous filter element in this embodiment. Typically, the third filter element 212 is fabricated of reticulated polyurethane foam and has about 5 pores per linear inch. It is noted that the third filter element 212 has a configuration which advantageously substantially surrounds the distal ends of the check valves 203–206. In this embodiment, the configuration of the third filter element 212 is such that wall thicknesses thereof are about 0.5 inch, while a height of a back and sides is about 1.5 inches. The third filter element has the effect of confining any effluent which passes through the check valves 203–206 so that the effluent material flow must pass through the filter elements 210–212 of the system 100 in order to traverse from the inlet ports 103–106 to the outlet stem 107.

The third filter element 212 may be fabricated in a "sofa" configuration as shown. Alternatively, the third filter element 212 can be fabricated from a flat sheet of material which is cut to shape and folded into the depicted shape.

It must be understood, of course, that the specific configurations and/or parameters of any of the filter elements 210–212 are desirable but can be varied in accordance with a specific filtration process required. In fact, some or all of the filter elements 210–212 may be combined or eliminated as a single filter element, if so desired.

Figure 3:
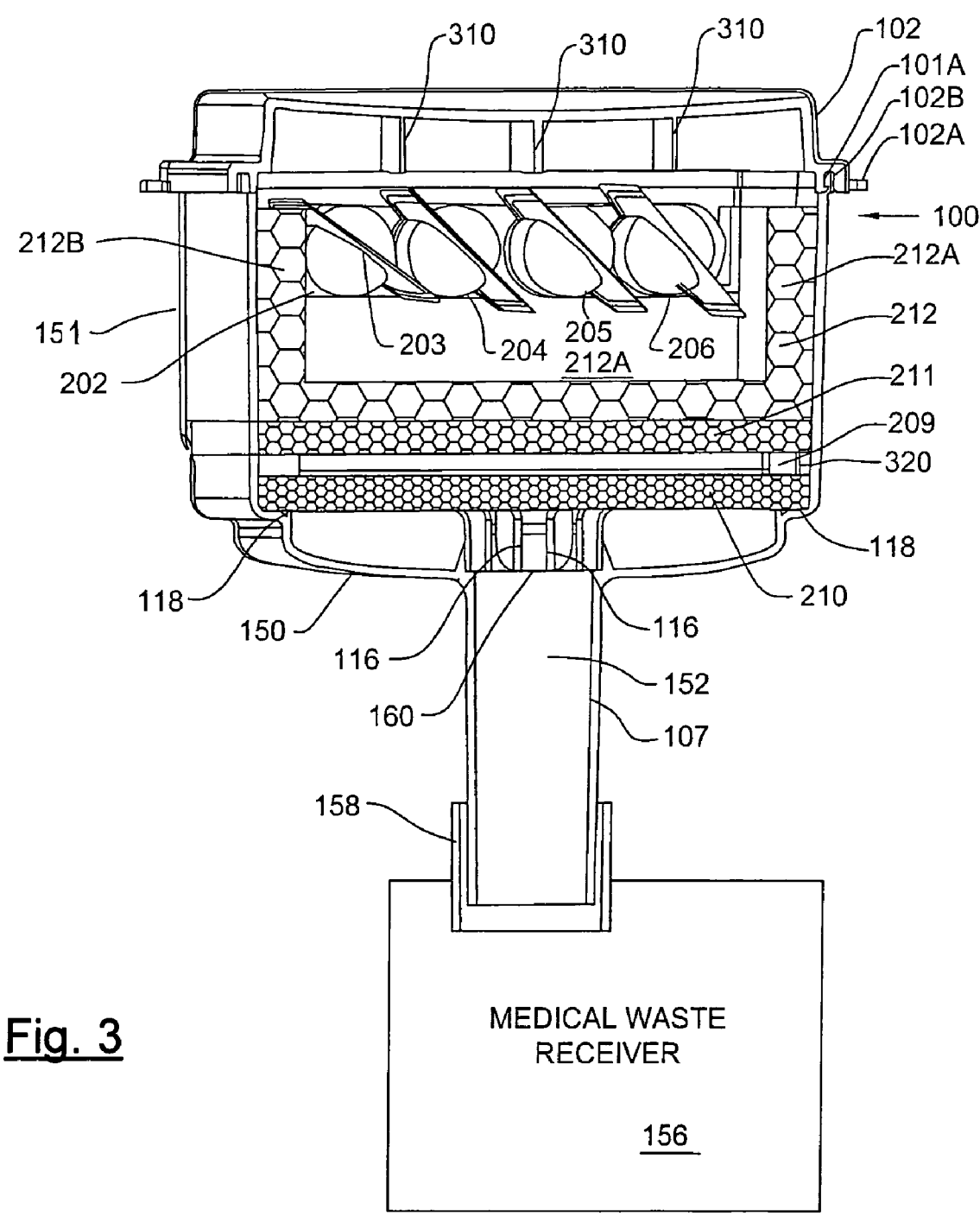
FIG. 3 is a partially broken away rear view of a preferred embodiment of the waste filter and manifold system of the instant invention.

Referring now to FIG. 3, there is shown a partially broken away view of the system 100 taken through a rear of the housing 101. There is shown an interior of the front surface of the housing 101 with the distal end of check valves 203–206 extending inwardly. The lid 102 includes the groove 102B which is secured to the edge 101A of the housing 101. Ribs 310 provide support and rigidity to the lid 102 and can be omitted in some designs.

As seen, the first filter element 10 is mounted adjacent the bottom of the housing 101 and above base opening 160 into outlet stem bore 152. A partial shading suggests a fine porosity of the first filter element 210. It is further observed that filter element 210 has a surface area greater than that of the cross sectional area of base opening 160.

The gasket 209 is disposed above the first filter element 210 and, as noted, is secured to the housing 101. In one embodiment, upright pins 320 extend upwardly from an inner bottom surface of the housing 101. The pins 320 extend through the first filter element 210 and engage apertures in the gasket 209 to secure the gasket 209 and the first filter element 210 to the housing 101. This arrangement maintains the first filter element 210 in position and affords a support for the other filter elements 211,212. The pins 320, if utilized, can be treated to assist in securing the gasket 209 to the housing 101.

The second filter element 211 rests upon the gasket 209 and, to some extent, upon the first filter element 210. The partial shading of second filter element 211 suggests a more porous structure than the first filter element 210.

The third filter element 212 is also provided in the housing 101 and is adjacent to the check valves 203–206. As shown, the third filter element 212 rests upon the second filter element 211 and substantially surrounds the distal ends of the check valves 203–206. That is, the third filter element 212 includes side walls 212A and 212B which extend upwardly along side walls of the housing 101 into close proximity to an inner surface of the lid 102. Thus, effluent from the check valves 203–206 is contained within the third filter element 212 to insure filtration of all of the effluent. The partial shading of the third filter element 212 suggests a structure which is more porous than the second filter element 211.

In FIG. 3, the support base 202 for the inlet ports 103–106 is shown although this support base 202 may be eliminated as described supra.

Figure 4:
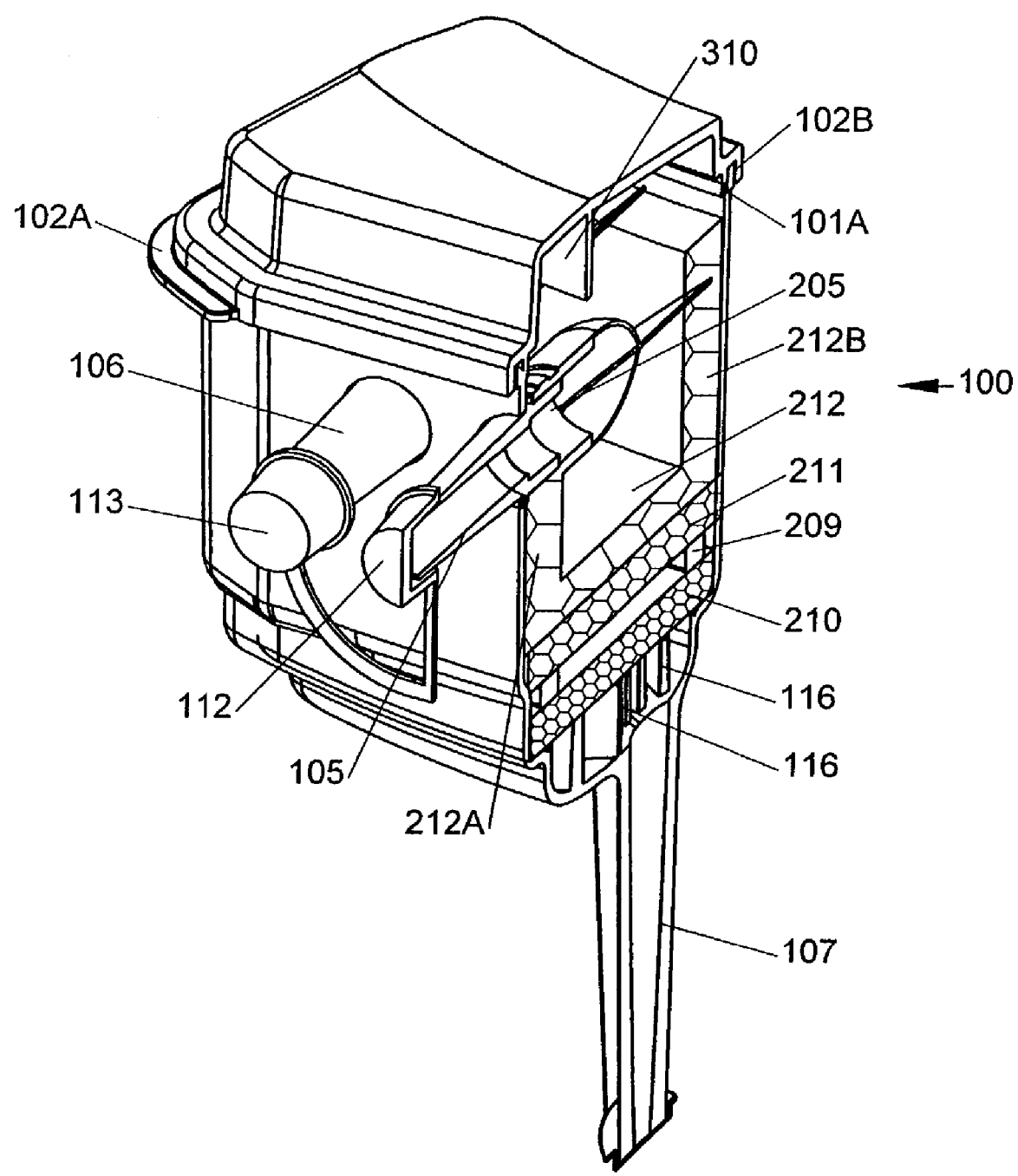
FIG. 4 is a partially broken away side or oblique view of the waste filter and manifold system shown in FIG. 3.

Referring now to FIG. 4, there is shown a cut away view of the system 100. The system 100 includes the housing 101, lid 102 and outlet port 107. Also, the inlet port 106 is shown complete while the inlet port 105 is partially broken away. The port cap 113 is shown along with the partially broken away port cap 112 together with the optional leash 109 and leash ring 108.

A partially cutaway view of the check valve 205 is shown inside the housing 101 and connected to the inlet port 105. The check valve 205 is described infra.

Ribs 116 (seen best in FIG. 5) are formed at a lower internal surface of the housing 101 extending toward base opening 160. The first filter element 210 rests upon an interior ledge 118 adjacent to the bottom of the housing 101 and, in some cases, upon upper edges of the ribs 116. The gasket 209 maintains the first filter element 210 in place as described supra. The second filter element 211 is supported by the gasket 209.

As seen in FIG. 4, the third filter element 212 rests on the second filter element 211. The third filter element 212 includes the side wall portions 212A and 212B which are joined to the bottom section of the third filter element 212. As noted supra, the third filter element 212 comprises a sofa-shaped, basket-like filter element which receives and filters all of the effluent from the check valves 203–206 before the flow passes through the other filter elements 210–211 and out through outlet port 107. The decreasing porosity of the filter elements 210–212 removes smaller sized, fluid borne matter as the fluid passes through the system 100.

Figure 5:
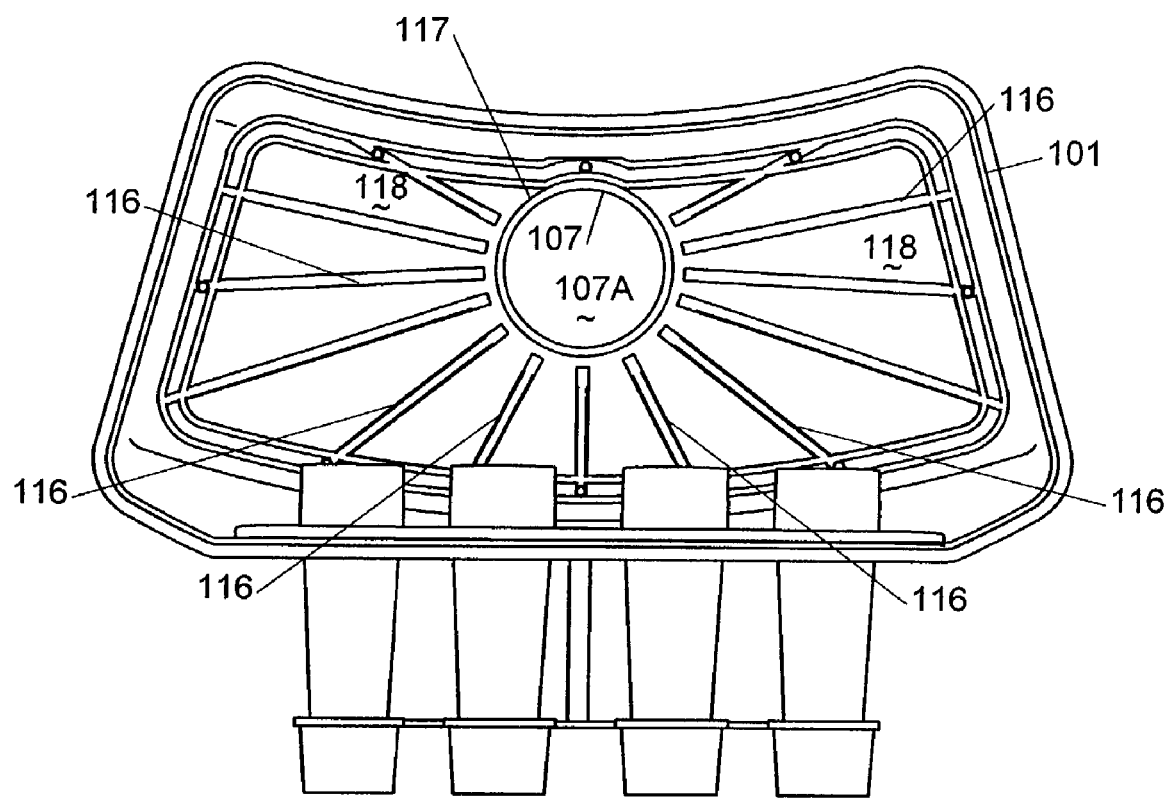
FIG. 5 is a top view of the housing for the waste filter and manifold system shown in FIG. 1 with the lid and the internal components removed.

Referring now to FIG. 5, there is shown a top view of the housing 101 with the lid 102 and the filter elements 210–212 removed. In this view, the inlet ports 103–106 are shown formed integrally with the housing 101 and with the check valves 203–206 removed. Housing base 150 is shown to incorporate a plurality of the ribs 116 which extend upwardly and generally radially from base opening 160 to the side walls of the manifold head. The ribs 116 serve to channel the effluent which has passed through the filter elements 210–212 into base opening 160. The rim 117 adjacent to base opening 160 manifold base 150 is sloped downwardly to enhance outward flow from the housing 101 to the outlet stem through bore 152. Manifold base 150 itself may also be configured to slope from the perimeter thereof toward opening 160 to enhance outward flow of effluent.

Referring now concurrently to FIGS. 6 and 7, there are shown an assembled view and an exploded view, respectively, of one of the check valves 203–206, for example. The check valve 203 comprises the connector tube 301 which is designed to engage with the respective inlet port 103. Typically, the tube 301 is a short cylindrical tube which is relatively rigid in order to maintain its shape. However, the tube 301 is able to snugly engage the inlet port 103 and form a secure, leakproof connection therewith.

The check valve 203 also includes an elongated, flattened tube 304 which is, in this embodiment, formed by flaps 302 and 303 of generally planar, flexible material such as PVC. The flaps 302 and 303 each have one end joined to the connector tube 301 in suitable fashion, as for example by adhesives, RF bonding, sonic welding or the like to form a secure seal. Side edges of the flaps 302 and 303 are also sealed to each other in a suitable fashion as suggested above. Thus, a common end of the flaps 302 and 303 along with the tube 301 forms a generally cylindrical opening which communicates with the space between the flaps which are sealed together at the side edges at seams 305 and 306 to form the flattened tube 304. The other ends of the flaps 302 and 303 are not sealed together but are independently flexible.

Thus, as shown in FIG. 8A, by properly selecting the dimensions of the components, the unsealed ends of the flaps 302 and 303 tend to come together snugly and form a closed end to the check valve 203.

Conversely, as shown in FIG. 8B, the unsealed ends of the flaps 302 and 303 can be spread apart by application of a modest force applied thereto by fluid passing through the check valve 203.

Thus, fluid can flow through the tube 301, through the channel in the tube 304 defined between the edge-sealed flaps 302 and 303, and out the unsealed end of the check valve 203. However, inasmuch as the unsealed ends of the flaps 302 and 303 tend to come together in the absence of a pressurized flow through the check valve 203 unidirectional flow is achieved and reverse flow through the check valve 203 cannot occur.

It should he understood that the pressurized flow can be provided by supplying a positive pressure at an input side of the connector tube 301 (e.g. via the inlet ports 103–106) or by supplying a negative pressure (e.g. vacuum) at the unsealed end of the flaps 302 and 303 at the distal end of the check valve 203 (e.g. via the outlet stem 107). In either case, unidirectional flow through the check valve 203 is achieved.

Thus, there is shown and described a unique design and concept of a waste filter and manifold system 100. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

What is claimed is:

1. A manifold for receiving medical waste, said manifold including:

a head, the head having a side wall assembly that defines an enclosed void space within said head, the void space having a cross-sectional area; a plurality of adjacent inlet ports, each inlet port configured to receive a separate tube through which medical waste is flowed; and a base that is a bottom-located structural member of said head, the base having a cross sectional area;

a stem that extends below said base, said stem having a cross sectional area less than the cross sectional area of said base so that the stem can be inserted in a conduit of a medical waste receiver; and a through bore, wherein said head base is formed with an opening between the head void space and the stem through bore, the base opening having a cross sectional area that is less than the cross sectional area of the head void space;

a filter member disposed in the head void space that extends upwardly against an interior surface of the side wall assembly to define within the head void space a hollow space, wherein said inlet ports each open directly into the hollow space;

a filter element disposed in the head void space that is above and spaced away from the base opening, that extends to and abuts the at least one interior surface of said head and that has a surface area, the surface area of said filter element being greater than the cross sectional area of the base opening; and a plurality of caps, each said cap shaped to selectively cover a separate one of the inlet ports, wherein each said cap is connected to said head by a tether.

2. The manifold of claim 1, wherein said filter element is a planar structure.

3. The manifold of claim 1, wherein said head base is shaped to slope downwardly to the base opening.

4. The manifold of claim 1, wherein a check valve is disposed in each said inlet port.

5. The manifold of claim 1, wherein each said inlet port is in the form of an elongated, open ended finger that extends away from said head.

6. The manifold of claim 1, wherein:
said head has a longitudinal center axis; and
said stem is centered along the longitudinal center axis of said head.

7. A manifold for use with a medical waste receiver, said manifold comprising:

a head having a top and a base opposite said top, said base having a cross sectional area; a side wall assembly extending between said base and said top, said base, said top and said side wall assembly having interior surfaces that collectively define a head void space having a cross sectional area, wherein said base is shaped to define an opening, the base opening having a cross sectional area, the cross sectional area of the base opening being less than the cross sectional area of the head void space;

a plurality of adjacent inlet ports that extend to said head, each said inlet port shaped to receive a tube through which medical waste is flowed, said inlet ports providing fluid communication from the tubes to said head;

a plurality of caps, said caps shaped to fit over and closing said inlet ports, each said cap being connected to said head by a tether;

a filter element disposed in the head void space that abuts at least one of the head interior surfaces and that is located above and over the base opening, said filter element having a surface area, the surface area of the filter element being greater than the surface area of the base opening;

a filter member disposed around the interior surface of the side wall assembly of said head to create a hollow space within the head void space, wherein each said inlet port opens directly into the hollow space; and a stem that extends downwards from said head base, said stem shaped to fit in a conduit of a medical waste receiver and having a cross sectional area less than the cross sectional area of the head base and bore that extends from said base opening through said stem.

8. The manifold of claim 7, wherein said filter element is a planar structure.

9. The manifold of claim 7, wherein said filter element extends to an interior surface of said head defined by said side wall assembly.

10. The manifold of claim 7, wherein said side wall assembly includes a plurality of wall panels.

11. The manifold of claim 7, wherein said head base is shaped to slope downwardly to the base opening.

12. The manifold of claim 7, wherein a check valve is disposed in each said inlet port.

13. The manifold of claim 7, wherein said inlet ports are elongated, open ended tubular fingers that extend from said head away from the hollow space, and each said finger is formed with an inlet bore into the hollow space.

14. The manifold of claim 7, wherein:
said head has a longitudinal center axis; and
said stem is centered along the longitudinal center axis of said head.

* * * * *